United States Patent [19]

Sircar

[11] 4,404,203
[45] Sep. 13, 1983

[54] SUBSTITUTED 6-PHENYL-3(2H)-PYRIDAZINONES USEFUL AS CARDIOTONIC AGENTS

[75] Inventor: Ila Sircar, Ann Arbor, Mich.

[73] Assignee: Warner-Lambert Company, Morris Plains, N.J.

[21] Appl. No.: 263,643

[22] Filed: May 14, 1981

[51] Int. Cl.$^3$ .................. C07D 237/14; C07D 237/04; C07D 237/24; A61K 31/50
[52] U.S. Cl. .................................... 424/250; 544/239
[58] Field of Search ........................ 424/250; 544/239

[56] References Cited

U.S. PATENT DOCUMENTS 4,107,315  8/1978  Lesher et al. ........................ 544/239

FOREIGN PATENT DOCUMENTS 884859  2/1981  Belgium .
54-19987  8/1979  Japan .
2057438  8/1980  United Kingdom .

OTHER PUBLICATIONS

Jahine et al., Pak. J. Sci. 30, 6–11, (1978).
17446 D/11 Derwent Abstract of Belgian Pat. No. 884,859, also enclosed.
Haginiwa, et al., Yakugaki Zasshi, 98, 67–71, (1978).
McEvoy, et al., J. Med. Chem., 17, 281 (1974).
Abstract of Germ. Pat. No. DT 2435-244.
Abstract of Ger. Pat. No. DT 2445-681.
William Curran et al., J. Med. Chem., 17, 273 (1974).
Luis Pitarch et al., Eur. Med. Chem. Chimica Therapeutica No. 6, 644 (1974).
Abstract of U.S. Pat. No. 4152-517.
Abstract of Japanese Pat. No. J51043-776.
Abstract of European Pat. No. EP 8391.
Abstract of European Pat. No. EP 10156.

*Primary Examiner*—Mark L. Berch
*Attorney, Agent, or Firm*—Walter Patton

[57] ABSTRACT

Substituted 6-phenyl-3(2H)-pyridazinone compounds are useful as cardiotonic agents.

Said compounds cause a significant increase in myocardial contractility in the anesthetized dog. Said compounds are produced by reacting substituted benzoylpropionic acids with suitably substituted hydrazines to provide 6-phenyl-4,5-dihydro-3(2H)-pyridazinones which are dehydrogenated to the desired product.

The intermediate 6-phenyl-4,5-dihydro-3(2H)-pyridazinones are themselves useful as cardiotonic agents.

3 Claims, No Drawings

SUBSTITUTED 6-PHENYL-3(2H)-PYRIDAZINONES USEFUL AS CARDIOTONIC AGENTS

BACKGROUND OF THE INVENTION

The present invention relates to 6-phenyl-3(2H)-pyridazinones and 6-phenyl-4,5-dihydro-3(2H)-pyridazinones useful as cardiotonic agents.

SUMMARY OF THE INVENTION

The present invention relates to novel substituted 6-phenyl-3(2H)-pyridazinone compounds useful as cardiotonic agents having the structural formula (I):

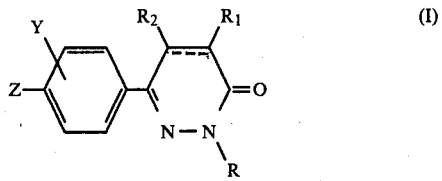

wherein ----- represents a double or single bond between two carbon atoms; R is hydrogen, lower alkyl, $-CH_2C_6H_5$ or $-C_6H_5$; and when $R_1$ is hydrogen, $R_2$ is $CF_3$, $-CH_2C_6H_5$, CN, $CO_2H$, $CON(R_3)_2$, $CH_2N(R_3)_2$, $-CH_2OH$, $N(R_3)_2$ and when $R_2$ is hydrogen, $R_1$ is $-CF_3$, $-CN$, $CON(R_3)_2$, $CH_2N(R_3)_2$, $N(R_3)_2$, $C_6H_5$ wherein $R_3$ is hydrogen or lower alkyl; with the proviso that both $R_1$ and $R_2$ are not hydrogen; Y and Z are hydrogen, halogen, lower alkyl, lower alkoxy, hydroxy, phenoxy or sulfonamido, wherein lower alkyl and lower alkoxy contain 1 to 3 carbon atoms; and the pharmaceutically acceptable salts thereof.

Further preferred novel compounds useful as cardiotonic agents are compounds having the structural formula II

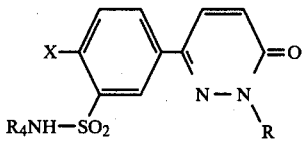

and the pharmaceutically acceptable salts thereof where R and $R_4$ are hydrogen or lower alkyl; and X is hydrogen or halogen.

The present invention also relates to 6-phenyl-4,5-dihydro-3(2H)-pyridazinones having the structural formula III where R, $R_1$, $R_2$, Y and Z are as defined above.

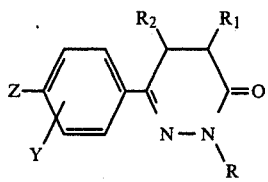

These compounds are not only useful as intermediates for preparing the compounds of formula I and II, but are also useful as cardiotonic agents.

The present invention further relates to the method for increasing cardiotonic contractility in a patient requiring such treatment which comprises administering orally or parenterally in a solid or liquid dosage form to such patient an effective amount of prior known compounds having the structure:

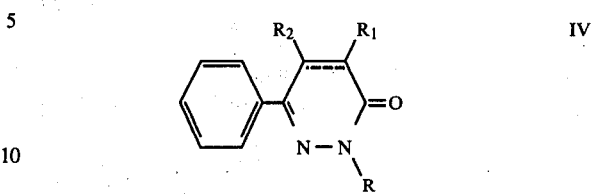

wherein ----- represents a double or single bond between two carbon atoms; when R and $R_1$ is hydrogen, $R_2$ is lower alkyl, $C_6H_5$; when R and $R_2$ are hydrogen; $R_1$ is hydrogen, $CO_2H$, $CH_2C_6H_5$, lower alkyl, $CH_2OH$; and when $R_1$ and $R_2$ are hydrogen, R is hydrogen, lower alkyl $CH_2C_6H_5$, $C_6H_5$, $CH_2CH_2N(CH_3)_2$,

The present invention further relates to the method for increasing cardiotonic contractility in a patient requiring such treatment which comprises administering orally or parenterally in a solid or liquid dosage form to such patient an effective amount of prior known and novel compounds having the structure:

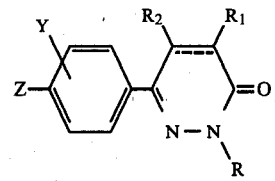

wherein ----- is a single or double bond between two carbon atoms; R is hydrogen, lower alkyl, $CH_2C_6H_5$, $C_6H_5$, $CH_2CH_2N(CH_3)_2$,

$R_1$ and $R_2$ are hydrogen, lower alkyl, $CO_2H$, $CH_2C_6H_5$, $CH_2OH$, $N(R_3)_2$, $CF_3$, $CON(R_3)_2$, CN, $CH_2N(R_3)_2$, $C_6H_5$; Y and Z are hydrogen, halogen, lower alkyl, lower alkoxy, hydroxy, phenoxy, sulfonamido or a pharmaceutically acceptable acid addition salt thereof.

Another aspect of the present invention relates to a cardiotonic composition for increasing cardiac contractility, said composition comprising an effective amount of the compound of formula (I) to (V) and a pharmaceutically acceptable carrier.

The present invention further relates to a method for increasing cardiac contractility which comprises the administration of a medicament comprising an effective amount of the compound of formula (I) to (V) and a pharmaceutically acceptable carrier.

The process for producing 6-phenyl-3(2H)-pyridazinones comprises reacting substituted benzoylpropionic acid with suitably substituted hydrazines to give 6-phenyl-4,5-dihydro-3(2H)-pyridazinones which can be dehydrogenated to the desired product by known dehydrogenation procedures such as bromination-dehydrobromination; by noble metal catalyzed dehydrogenation such as palladium catalyzed dehydrogenation or by oxidation-reduction procedures using m-nitrobenzene sulphonic acid as the reagent according to the standard literature procedure set forth in W. V. Curran and Adma Ross, J. Med. Chem., 17, 273 (1974).

The compounds of formulas (I) to (V) are useful both in the free base form and in the form of acid addition salts; and, both forms are within the scope of the invention. The acid addition salts are a more convenient form for use; and in practice, use of the salt form amounts to use of the base form. In practicing the invention, it was found convenient to form the sulfate, phosphate or methanesulfonate. However, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid and the like, giving the hydrochloride, sulfamate, ethanesulfonate, benzenesulfonate, p-toluenesulfonate and the like respectively.

The acid addition salts of said basic compounds are prepared either by dissolving the free base in aqueous or aqueous alcohols solution or other suitable solvents containing the appropriate acid and isolating the salt by evaporating the solution, or by reacting the free base and acid in an organic solvent, in which case the salt separates directly or can be obtained by concentration of the solution.

The following examples will further illustrate the invention without, however, limiting it thereto.

EXAMPLE 1

Preparation of 6-phenyl-3(2H)-pyridazinone

A mixture of 3-benzoylpropionic acid (89 g), 80% hydrazine hydrate (25.5 ml) in ethanol (1000 ml) is refluxed for 6 hrs, cooled and filtered to give 75.6 g of 6-phenyl-4,5-dihydro-3(2H)-pyridazinone. Bromine (70 g) is added dropwise to a solution of the above pyridazinone in acetic acid (200 ml) at 80° C. After the addition is over, the mixture is heated to 100° C. for 15 minutes, cooled, filtered and washed with isopropyl ether. The solid is slurried in water, adjusted to pH 10 and filtered to give 60 g of the product 6-phenyl-3(2H)-pyridazinone.

Ref: A. Lespagnol and J. Deprey, Bull. Soc. Chim., 1962, 1117.

The following compounds are prepared according to the procedure set forth in Example 1: 6-(4-fluorophenyl)-3(2H)-pyridazinone; 6-(4-chlorophenyl)-3(2H)-pyridazinone; 6-(3,4-dichlorophenyl)-3(2H)-pyridazinone; 6-(3,4-dimethoxyphenyl)-3(2H)-pyridazinone; 6-(3,4-dihydroxyphenyl)-3(2H)-pyridazinone; 6-(4-methylphenyl)-3(2H)-pyridazinone; 6-(4-phenoxyphenyl)-3(2H)-pyridazinone; 5-methyl-6-phenyl-3(2H)-pyridazinone; 5,6-diphenyl-3(2H)-pyridazinone; 4-methyl-6-phenyl-3(2H)-pyridazinone; 2-methyl-6-phenyl-3(2H)-pyridazinone; 2,6-diphenyl-3(2H)-pyridazinone; and 2-benzyl-6-phenyl-3(2H)-pyridazinone.

EXAMPLE 2

6-(4-Chloro-3-sulfonamidophenyl)-3(2H)-pyridazinone 6-(4-Chlorophenyl)-3(2H)-pyridazinone (20.4 g) [*Eur. J. Med. Chem.*, 644, (1974)] is added to 70 ml of chlorosulfonic acid with stirring. The solution is heated under reflux for 2 hours, cooled, and poured into ice water. The solid is filtered, washed with water and added to 250 ml of liquor ammonia. The residue obtained after evaporation of the liquor ammonia is treated with water filtered, washed with water, and crystallized from acetic acid to give 2-chloro-5-(1,6-dihydro-6-oxo-3-pyridazinyl)benzenesulfonamide.

Similarly reaction of 2-methyl-6-(4-chlorophenyl)-3(2H)-pyridazinone with chlorosulfonic acid followed by ammonia according to the procedure of this Example gives 2-chloro-5-(1,6-dihydro-1-methyl-6-oxo-3-pyridazinyl)benzenesulfonamide.

Similarly reaction of 2-methyl-6-(4-chlorophenyl)-3(2H)-pyridazinone with chlorosulfonic acid followed by methylamine according to the procedure of this Example gives 2-chloro-5-(1,6-dihydro-1-methyl-6-oxo-3-pyridazinyl)-N-methylbenzenesulfonamide.

EXAMPLE 3

4-(Dimethylaminomethyl)-6-phenyl-3(2H)-pyridazinone

A mixture of 2-benzyl-6-phenyl-4,5-dihydro-3(2H)-pyridazinone (23.9 g) paraformaldehyde (5.0 g), and dimethylamine hydrochloride (8.0 g) in 200 ml of ethanol is heated under reflux for 4 hours. The ethanol is removed by distillation on the rotary evaporator and the residue is rendered basic with ammonium hydroxide solution. This is extracted with dichloromethane. The dichloromethane is concentrated on the rotary evaporator and the residue is chromatographed on silica gel with 2% methanol/chloroform to give 2-benzyl-4-(dimethylaminomethyl)-6-phenyl-4,5-dihydro3(2H)-pyridazinone. This is dissolved in 500 ml of methanol and catalytically hydrogenated at 3 atmospheres pressure over 5% paladium on charcoal. The catalyst is removed by filtration and the methanol is concentrated to give 4-(dimethylaminomethyl)-6-phenyl-4,5-dihydro-3(2H)-pyridazinone. This compound is treated with bromine in acetic acid according to the procedure of Example 1 to give 4-(dimethylaminomethyl)-6-phenyl-3(2H)-pyridazinone.

EXAMPLE 4

2,3-Dihydro-3-oxo-6-phenyl-4-pyridazinecarboxamide

A. A mixture of 2,3-dihydro-3-oxo-6-phenyl-4-pyridazinecarboxylic acid (1.92 g) ethyl chloroformate (1.1 g) and triethylamine (2.0 ml) in 50 ml of dichloromethane is allowed to stir at 25°–30° C. for 2 hours. Ammonia gas is then bubbled into the mixture for 15 minutes. Water (50 ml) is added and the dichloromethane is separated and concentrated on the rotary evaporator. The residue is chromatographed on silica gel with 2% methanol and chloroform to give 2,3-dihydro-3-oxo-6-phenyl-4-pyridazinecarboxamide.

B. In an alternate procedure, a mixture of 2,3-dihydro-3-oxo-6-phenyl-4-pyridazinecarboxylic acid (1.92 g), triethylamine (3.0 ml), and thionyl chloride (5.0 ml) in tetrahydrofuran is allowed to stir at 20°–25° C. for 6 hours. The mixture is concentrated on the rotary evaporator and the residue is treated with 50 ml of cold ammonium hydroxide solution. The solid product is collected and recrystallized from acetic acid to give 2,3-dihydro-3-oxo-6-phenyl-4-pyridazinecarboxamide.

Similarly, reaction of either 2,3-dihydro-3-oxo-6-(4-chloro-3-sulfonamidophenyl)-4-pyridazinecarboxylic acid or 2,3-dihydro-3-oxo-6-(3,4-dimethoxyphenyl)-4-pyridazinecarboxylic acid according to the procedures described in this Example gives: 2,3-dihydro-3-oxo-6-(4-chloro-3-sulfonamidophenyl)-4-pyridazinecarboxamide, and 2,3-dihydro-3-oxo-6-(3,4-dimethoxyphenyl)-4-pyridazinecarboxamide.

EXAMPLE 5

2,3-Dihydro-3-oxo-6-phenyl-4-pyridazinecarbonitrile

A mixture of 2,3-dihydro-3-oxo-6-phenyl-4-pyridazincarboxamide (4.2 g) in 100 ml of acetic anhydride is heated under reflux for 6 hours. The acetic anhydride is removed by distillation and the residue is partitioned between ammonium hydroxide solution and dichloromethane. The dichloromethane layer is separated and concentrated on the rotary evaporator and the residue is recrystallized from ethanol to give 2,3-dihydro-3-oxo-6-phenyl-4-pyridazinecarbonitrile.

Similarly, reaction of 2,3-dihydro-3-oxo-6-(4-chloro-3-sulfonamidophenyl)-4-pyridazinecarboxamide or 2,3-dihydro-3-oxo-6-(3,4-dimethoxyphenyl)-4-pyridazinecarboxamide with acetic anhydride according to the procedure of this Example gives: 2,3-dihydro-3-oxo-6-(4-chloro-3-sulfonamidophenyl)-4-pyridazinecarbonitrile and 2,3-dihydro-3-oxo-6-(3,4-dimethoxyphenyl)-4-pyridazinecarbonitrile.

EXAMPLE 6

6-Phenyl-4 and 5-trifluoromethyl-3(2H)-pyridazinone

To a solution of α-phenyl-4-morpholinoacetonitrile (J. D. Albright, et al., J. Heterocyclic Chem., 881, 1978) (20.3 g) in 20 ml of tetrahydrofuran is added 5 ml of 30% potassium hydroxide in methanol followed by ethyl 2-trifluoromethylacrylate (16.8 g). After stirring at room temperature for 18 hours, the solvent is concentrated on the rotary evaporator. The residue is hydrolyzed in 70% acetic acid (40 ml) to give 2-trifluoromethyl-3-(benzoyl)propionic acid. Treatment of this acid with hydrazine hydrate according to the procedure of Example 1 gives 6-phenyl-4-trifluoromethyl-4,5-dihydro-3(2H)-pyridazinone. Reaction of this compound with bromine in acetic acid according to Example 1 affords 6-phenyl-4-trifluoromethyl-3(2H)-pyridazinone.

In the same manner, reaction of α-phenyl-4-morpholinoacetonitrile with ethyl 3-trifluoromethylacrylate, followed by treatment of the resulting 3-trifluoromethyl-3-(benzoyl)propionic acid with hydrazine hydrate gives 6-phenyl-5-trifluoromethyl-4,5-dihydro-3(2H)-pyridazinone.

Similarly, reaction of this dihydro-3(2H)-pyridazinone with bromine in acetic acid according to the procedure of Example 1 gives: 6-phenyl-5-trifluoromethyl-3-(2H)-pyridazinone.

EXAMPLE 7

2,3-Dihydro-3-oxo-6-phenyl-5-pyridazinecarbonitrile

A solution of ethyl-α-cyano-γ-oxo-phenylpropanoate (21.8 g) in 100 ml of dry tetrahydrofuran is added dropwise over 0.5 hours to a stirred mixture of sodium hydride (2.4 g) in 100 ml of tetrahydrofuran followed by ethyl bromoacetate (16.7 g) in 100 ml of tetrahydrofuran. After stirring for 6 hours, the mixture is heated under reflux for 12 hours, then cooled, and concentrated on the rotary evaporator. The residue is treated with 200 ml of 20% potassium hydroxide in methanol and 20 ml of water and allowed to stir overnight. The methanol is removed on the rotary evaporator and the residue is diluted with 200 ml of water. Acetic acid is added to adjust the pH to 6 and the mixture is heated under reflux for 6 hours. Upon cooling, the aqueous mixture is again adjusted to pH 6 and β-cyano-γ-oxo-phenylbutanoic acid is collected. This acid is reacted with hydrazine hydrate according to the procedure in Example 1 to give 2,3,4,5-tetrahydro-3-oxo-6-phenyl-5-pyridazinecarbonitrile. This is reacted with acetic acid in bromine according to the procedure of Example 1 to give 2,3-dihydro-3-oxo-6-phenyl-5-pyridazinecarbonitrile.

EXAMPLE 8

2,3-Dihydro-3-oxo-6-phenyl-5-pyridazinecarboxylic acid

A mixture of 2,3-dihydro-3-oxo-6-phenyl-5-pyridazinecarbonitrile (10.0 g) in 30% sulfuric acid (100 ml) is heated under reflux for 24 hours. Upon cooling, the pH of the solution is adjusted to 6 with ammonium hydroxide to give 2,3-dihydro-3-oxo-6-phenyl-5-pyridazinecarboxylic acid.

EXAMPLE 9

2,3-Dihydro-3-oxo-6-phenyl-5-pyridazinecarboxamide 2,3-Dihydro-3-oxo-6-phenyl-5-pyridazinecarbonitrile (10.0 g) is added to cold (0°–5° C.) concentrated sulfuric acid (50 ml) and the resulting solution is kept at 0°–5° C. for 24 hours and then poured onto crushed ice and the solid product is collected and recrystallized from aqueous ethanol to give 2,3-dihydro-3-oxo-6-phenyl-5-pyridazinecarboxamide.

EXAMPLE 10

5-(Dimethylaminomethyl)-6-phenyl-3(2H)-pyridazinone 2,3-Dihydro-3-oxo-6-phenyl-5-pyridazinecarboxylic acid is treated with ethyl chloroformate, triethylamine, and dimethylamine according to the procedure of Example 3 to give N,N-dimethyl-2,3-dihydro-3-oxo-6-phenyl-5-pyridazinecarboxamide. A solution of this amide (12.5 g) in 400 ml of tetrahydrofuran is treated with 100 ml of 1 M borane in tetrahydrofuran and the resulting mixture is heated under reflux for 4 hours, then cooled and treated with 5% sodium hydroxide (100 ml) and heated under reflux for 1 hour. The tetrahydrofuran is removed on the rotary evaporator and the pH of the residual liquid is adjusted with acetic acid followed by ammonium hydroxide to 10. The product is extracted into dichloromethane and the dichloromethane is filtered and concentrated on the rotary evaporator. The residue is chromatographed on silica gel with 2% methanol and chloroform to give 5-(dimethylaminomethyl)-6-phenyl-3(2H)-pyridazinone.

EXAMPLE 11

5-Amino-6-phenyl-3(2H)-pyridazinone

Bromine (5.75 ml) is added to a solution of 2,3-dihydro-3-oxo-6-phenyl-5-pyridazinecarboxamide (2.0 g) and sodium hydroxide (15 g) in 250 ml of water while holding the internal temperature at 0°–5° C. The mixture is heated on a steam bath for 5 hours, cooled, and the pH adjusted to 7 with aqueous sodium bicarbonate. The product is collected and recrystallized from aqueous ethanol to give 5-amino-6-phenyl-3(2H)-pyridazinone.

Similarly, treatment of 2,3-dihydro-3-oxo-6-phenyl-4-pyridazinecarboxamide with bromine and sodium hydroxide affords 4-amino-6-phenyl-3(2H)-pyridazinone.

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and blood pressure. This test procedure is described in the following paragraphs.

Test for in vivo Myocardial Inotropic Activity in Anesthetized Dog

This screen consists of determining the effects of increasing intravenous doses of compound on myocardial contractility (dp/dT max of left ventricular blood pressure), heart rate and aortic blood pressure of the pentobarbital-anesthetized dog.

Methods

Adult mongrel dogs of either sex are anesthetized with pentobarbital, 35 mg/kg, i.v., and are subsequently maintained under anesthesia with a continuous infusion of pentobarbital, 3.5 mg/kg/hr. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip recorder. Heart rate, using a biotachometer triggered from the R wave of the ECG, and the first derivative of left ventricular blood pressure (dp/dT), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0 N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention when administered intravenously at a rate of about 0.1 to 1.0 mg/kg/min cause dose related significant increases in cardiac contractility with only low or minimal changes in heart rate and blood pressure.

Test Results of 6-Phenyl-3(2H)—pyridazinone Using Anesthetized Dog Procedure % CHANGE

| CPD, DOSE MG/KG (n = 2) | MYOCARDIAL CONTRACTILITY | HEART RATE | BLOOD PRESSURE |
|---|---|---|---|
| 0.1 | 9.2 | −4 | −2.2 |
| 0.31 | 21.7 | +7.5 | +2.2 |
| 1.0 | 50.5 | +18.5 | +9.6 |

The actual determination of the numerical cardiotonic data definitive for any other particular compound of the invention is readily obtained according to the above-described standard test procedure by those skilled in pharmacological test procedures, without any need for any extensive experimentation.

The present invention includes within its scope a cardiotonic composition for increasing cardiac contractility, said composition comprising a pharmaceutically acceptable carrier and, as the active component thereof, a cardiotonic compound of the present invention or pharmaceutically acceptable acid addition salt thereof. The invention also includes within its scope the method for increasing cardiac contractility in a patient requiring such treatment which comprises administering to such patient an effective amount of a compound of the present invention or pharmaceutically acceptable acid addition salt thereof. In clinical practice the said compounds of the present invention will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents such as magnesium stearate, talc and the like.

Liquid compositions for oral administration include pharmaceutically acceptable emulsions, solutions, suspensions, syrups and elixirs containing inert diluents commonly used in the art, such as water or liquid paraffin. Besides inert diluents such compositions may also contain adjuvants, such as wetting and suspending agents, and sweetening, flavoring, perfuming and preserving agents. According to the invention, the compounds pounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example by filtration through a bacteria-retaining filter, by incorporation of sterilizing agents in the compositions, by irradiation or by heating. They may also be manufactured in the form of sterile solid compositions which can be dissolved in sterile water or some sterile injectable medium immediately before use.

The percentage of active component in the said composition and method for increasing cardiac contractility may be varied so that a suitable dosage is obtained. The dosage administered to a particular patient is variable, depending upon the clinician's judgement using as the criteria: The route of administration, the duration of treatment, the size and condition of the patient, the potency of the active component and the patient's response thereto. An effective dosage amount of active component can thus only be determined by the clinician considering all criteria and utilizing his best judgement on the patient's behalf.

What is claimed is:

1. A compound having the structural formula:

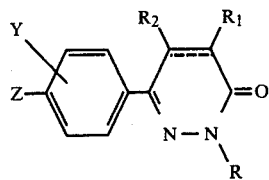

wherein ===== represents a double or single bond between two carbon atoms; R is hydrogen, lower alkyl, —CH$_2$C$_6$H$_5$ or —C$_6$H$_5$; and when R$_1$ is hydrogen, R$_2$ is CF$_3$, —CH$_2$C$_6$H$_5$, CN, CO$_2$H, CON(R$_3$)$_2$, CH$_2$N(R$_3$)$_2$, —CH$_2$OH, N(R$_3$)$_2$, and when R$_2$ is hydrogen, R$_1$ is —CF$_3$, —CN, CON(R$_3$)$_2$, CH$_2$N(R$_3$)$_2$, N(R$_3$)$_2$, wherein R$_3$ is hydrogen or lower alkyl; Y and Z are hydrogen, halogen, lower alkyl, lower alkoxy, hydroxy, phenoxy, sulfonamido; wherein lower alkyl and lower alkoxy contain 1 to 3 carbon atoms; and the pharmaceutically acceptable acid addition salts thereof.

2. A compound having the structural formula:

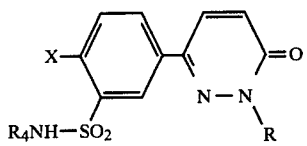

and the pharmaceutically acceptable salts thereof where R and R$_4$ are hydrogen or lower alkyl; and X is hydrogen or halogen.

3. The method for increasing cardiotonic contractility in a patient requiring such treatment which comprises administering orally or parenterally in a solid or liquid dosage form in a pharmaceutically acceptable carrier to such a patient an effective amount of a compound having the structure:

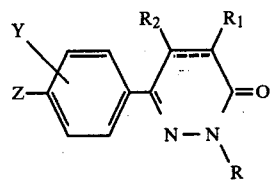

wherein ===== represents a single or double bond between two carbon atoms; R is hydrogen, lower alkyl, —CH$_2$C$_6$H$_5$ or —C$_6$H$_5$; and when R$_1$ is hydrogen, R$_2$ is CF$_3$, CN, CO$_2$H, CON(R$_3$)$_2$, CH$_2$N(R$_3$)$_2$, —CH$_2$OH, N(R$_3$)$_2$, and when R$_2$ is hydrogen, R$_1$ is —CF$_3$, —CN, CON(R$_3$)$_2$, CH$_2$N(R$_3$)$_2$, N(R$_3$)$_2$, wherein R$_3$ is hydrogen or lower alkyl Y and Z are hydrogen, halogen, lower alkyl, lower alkoxy, hydroxy, phenoxy, sulfonamido; wherein lower alkyl and lower alkoxy contain 1 to 3 carbon atoms; and the pharmaceutically acceptable acid addition salts thereof.

* * * * *